(12) United States Patent
Kristen et al.

(10) Patent No.: US 12,151,083 B2
(45) Date of Patent: Nov. 26, 2024

(54) SELF-SEALING SEPTUM

(71) Applicant: Roche Diabetes Care, Inc., Indianapolis, IN (US)

(72) Inventors: Thomas Kristen, Mannheim (DE); Olaf Lebau, Mannheim (DE)

(73) Assignee: Roche Diabetes Care, Inc., Indianapolis, IN (US)

( * ) Notice: Subject to any disclaimer, the term of this patent is extended or adjusted under 35 U.S.C. 154(b) by 591 days.

(21) Appl. No.: 16/797,598

(22) Filed: Feb. 21, 2020

(65) Prior Publication Data

US 2020/0188582 A1 Jun. 18, 2020

Related U.S. Application Data

(63) Continuation of application No. PCT/EP2018/072330, filed on Aug. 17, 2018.

(30) Foreign Application Priority Data

Aug. 22, 2017 (EP) ..................................... 17187167
Dec. 20, 2017 (EP) ..................................... 17209081

(51) Int. Cl.
*A61M 5/162* (2006.01)
*A61J 1/06* (2006.01)
(Continued)

(52) U.S. Cl.
CPC ........ *A61M 5/162* (2013.01); *A61M 39/0208* (2013.01); *A61M 2039/0054* (2013.01);
(Continued)

(58) Field of Classification Search
CPC .............. A61M 5/162; A61M 39/0208; A61M 2039/0054; A61M 2039/0072;
(Continued)

(56) References Cited

U.S. PATENT DOCUMENTS

| 4,802,885 A | 2/1989 | Weeks et al. |
| 5,676,346 A | 10/1997 | Leinsing |

(Continued)

FOREIGN PATENT DOCUMENTS

| EP | 2 528 642 A2 | 12/2012 |
| EP | 3 028 737 A1 | 6/2016 |

(Continued)

OTHER PUBLICATIONS

International Preliminary Report on Patentability, PCT/EP2018/072330, Oct. 22, 2019, 7 pages.
(Continued)

*Primary Examiner* — Robert J Utama
*Assistant Examiner* — Hamza A Darb
(74) *Attorney, Agent, or Firm* — Bose McKinney & Evans LLP

(57) ABSTRACT

Disclosed herein is a pierceable elastic septum for use in drug reservoirs and infusion sets, the pierceable septum comprising a first surface and a second surface. The first surface and the second surface are positioned opposite to each other. A distance between the first surface and the second surface is not constant over the first surface, and is configured such that if a higher pressure is applied to the first surface as compared to the second surface, a component of a force, which is exerted on the first surface, acts towards an axis (A) which intersects the center of the first surface and the center of the second surface.

24 Claims, 9 Drawing Sheets

(51) Int. Cl.
  *A61J 1/14* (2023.01)
  *A61M 39/00* (2006.01)
  *A61M 39/02* (2006.01)

(52) U.S. Cl.
  CPC .............. *A61M 2039/0072* (2013.01); *A61M 2039/0081* (2013.01)

(58) Field of Classification Search
  CPC ........ A61M 2039/0081; A61M 5/2455; A61M 5/2466; A61M 2005/247; A61M 2005/2474; A61M 5/288; A61M 2039/027; A61M 2039/1072; A61M 2039/0288; A61M 39/20; A61M 39/221; A61M 2205/19; B32B 2307/54; B32B 2535/00; B32B 7/022; B32B 2250/03; B32B 3/263; B32B 3/30; B32B 15/06; B32B 15/08; B32B 25/042; B32B 25/08; B32B 25/12; B32B 25/20; B32B 27/08; B32B 27/40; B32B 2307/51; B32B 2307/536; A61J 1/201; A61J 2200/10; A61J 1/062; A61J 1/1406; A61J 1/2006; A61J 1/2027; A61J 1/2013; A61J 1/2017; B65B 3/003
  See application file for complete search history.

(56) References Cited

U.S. PATENT DOCUMENTS

| | | | | |
|---|---|---|---|---|
| 5,678,713 | A | * | 10/1997 | Derksen ............... B65D 51/002 215/254 |
| 2002/0082586 | A1 | * | 6/2002 | Finley .................. A61M 39/045 604/533 |
| 2004/0236274 | A1 | | 11/2004 | Reinmann et al. |
| 2006/0127246 | A1 | * | 6/2006 | Forsell .............. A61M 39/0208 417/412 |
| 2007/0078391 | A1 | | 4/2007 | Wortley et al. |
| 2012/0296290 | A1 | | 11/2012 | Argauer et al. |
| 2013/0116664 | A1 | | 5/2013 | Tai et al. |
| 2015/0164745 | A1 | * | 6/2015 | Gobbi Frattini .......... A61J 1/22 604/407 |
| 2016/0015958 | A1 | * | 1/2016 | Ueda ..................... A61M 39/26 604/537 |
| 2016/0199560 | A1 | | 7/2016 | Casiello et al. |
| 2017/0071826 | A1 | * | 3/2017 | Py ......................... A61J 1/1406 |

FOREIGN PATENT DOCUMENTS

| | | |
|---|---|---|
| WO | WO 97/01370 A1 | 1/1997 |
| WO | WO 02/07804 A1 | 1/2002 |
| WO | WO 03/020360 A1 | 3/2003 |
| WO | WO 2006/116438 A2 | 11/2006 |
| WO | WO 2012/101101 A1 | 8/2012 |
| WO | WO 2016/141082 A1 | 9/2016 |
| WO | WO 2018/132540 A1 | 7/2018 |

OTHER PUBLICATIONS

International Search Report and Written Opinion of the International Searching Authority, PCT/EP2018/072330, Nov. 30, 2018, 13 pages.

* cited by examiner

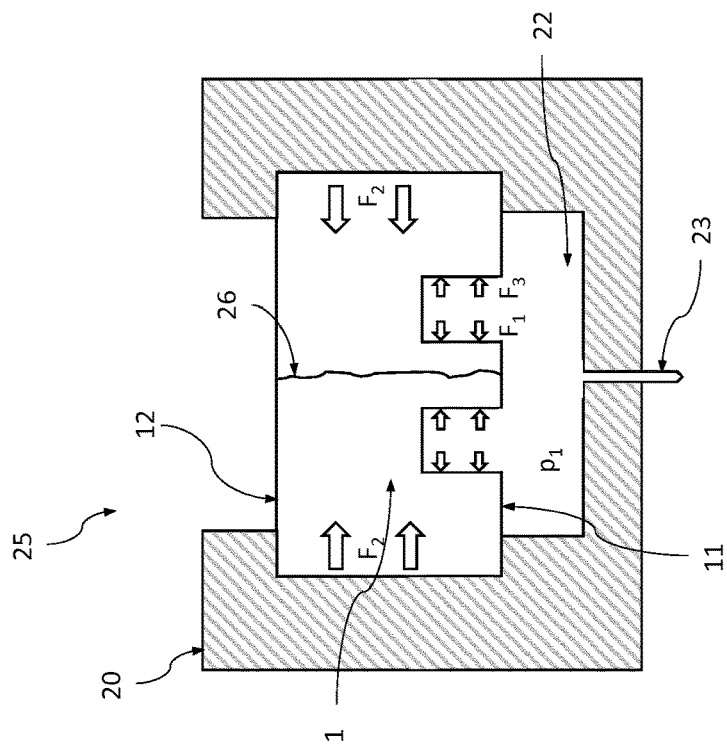
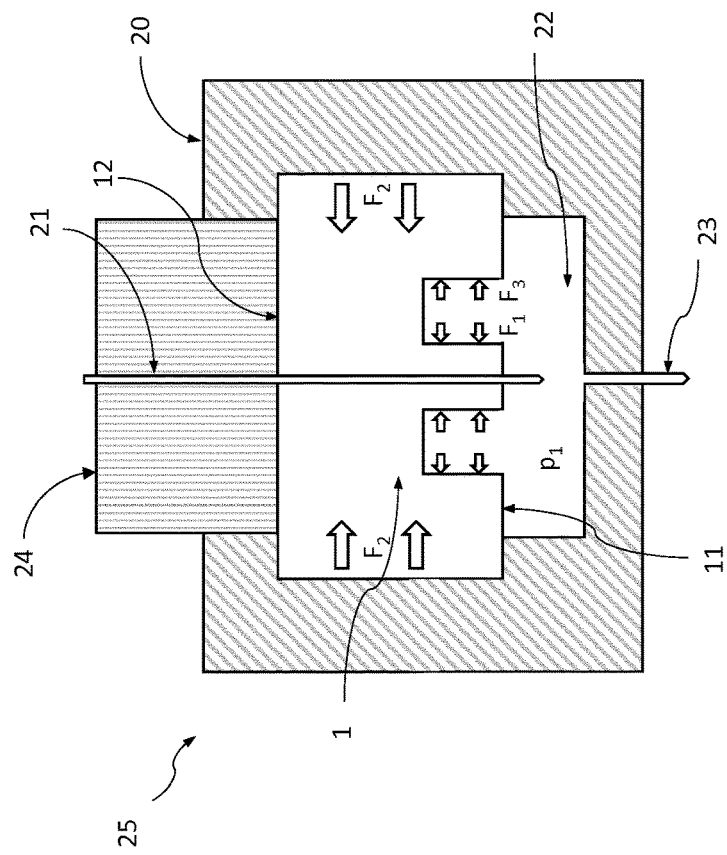
Figure 10 (a)
Figure 10 (b)

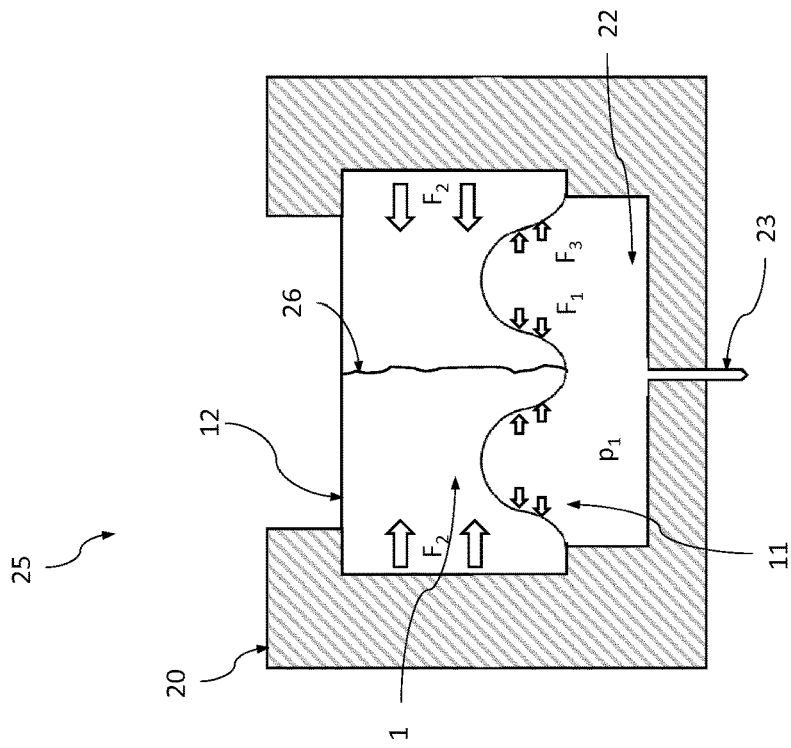
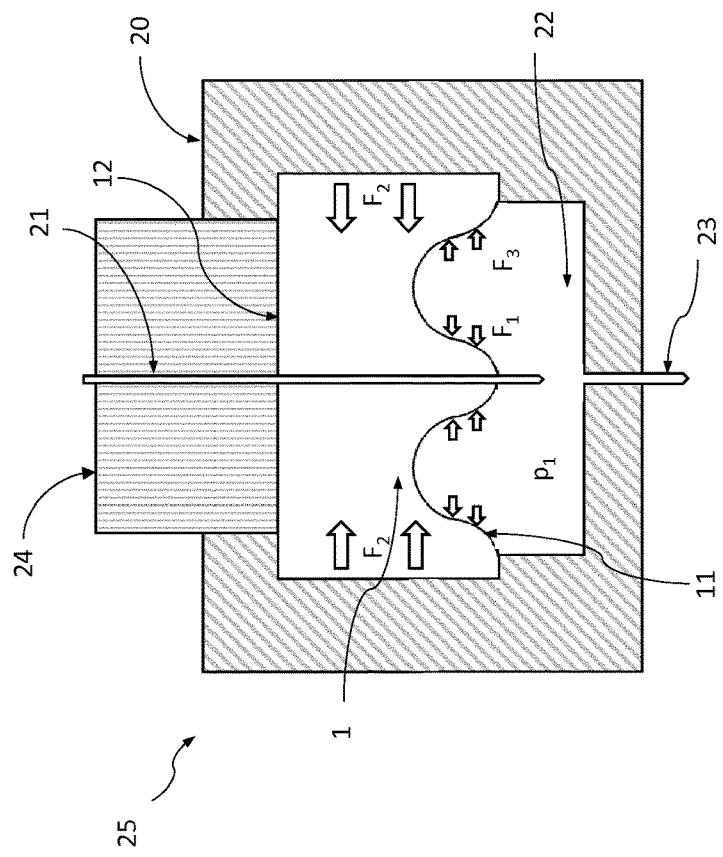

SELF-SEALING SEPTUM

RELATED APPLICATIONS

This application is a continuation of PCT/EP2018/072330, filed Aug. 17, 2018, which claims priority to EP 17 187 167.6, filed Aug. 22, 2017, and EP 17 209 081.3, filed Dec. 20, 2017, all of which are incorporated herein by reference in their entirety.

BACKGROUND

This disclosure lies in the field of infusion or injection technology. More particularly, it is related to septa as used in infusion sets or reservoirs for liquid drugs, to infusion sets and reservoirs comprising a septum, as well as the use of a septum in an infusion set or reservoir.

Ambulatory infusion sets are well known in the art. For example in the in the therapy of Diabetes Mellitus they are used in combination with a miniaturized infusion pump for Continuous Subcutaneous Insulin Infusion (CSII) where small drug amounts are infused in a metered way via a cannula into the tissue of a patient. Such infusion sets can also be used in a number of further therapies, such as pain therapy or cancer therapy. They are available from a number of suppliers, such as Roche Diabetes Care GmbH, Germany, or Medtronic MiniMed Inc., CA, USA. For example in CSII, the metered doses are in the range of microliters or nanoliters.

Although typical infusion sets and infusion systems are usually operated in a continuous manner and thus constantly carried by the patient, there are several daily routines, such as showering, swimming, etc. in which the pump and the tubing should be removed. In such events, it is in the interest of the patient and favorable for cost reasons that the cannula unit remains on the patient so that the flexible infusion cannula used to introduce drug into the patient's tissue is not removed. Therefore, infusion systems have been developed, comprising cannula units which can be easily disconnected from the remaining parts, in particular a tubing, by disconnection of a connector device. The connector device comprises a connector cannula, which is fluidly connected to a tubing and an infusion pump. However, upon each reconnection, the septum of the cannula unit is pierced by the connector cannula. As a result, the septum suffers multiple cuts by the commonly employed sharp cannulas and therefore becomes more prone to leakage.

A wide variety of infusion sets for introducing a liquid drug into a patient's body rely on elastic septa, which may be pierced multiple times by a cannula or a needle. A typical infusion set can for example comprise a cannula unit, which can be fluidly connected to an infusion pump and/or a drug reservoir via a tubing with a connector device that has a connector cannula. Typically the cannula unit further comprises a compartment for a liquid drug, which is at least partially formed by a surface of a septum. In particular, the septum may be used for sealing this compartment which is essentially in permanent fluid connection to the patient's tissue via an infusion cannula. In such systems, liquid drug can be transferred to the compartment and subsequently to the patient via the connector cannula and the infusion cannula.

Furthermore in regard to infusion sets, it is advantageous to employ flexible infusion cannulas for establishing a permanent fluid connection to the patient's tissue. Such flexible infusion cannulas are inserted into the patient's tissue with the help of a piercing needle, such as a rigid steel needle, a section of which is initially arranged within a lumen of the infusion cannula, while a head section is arranged above the septum and the piercing needle penetrates the septum. After insertion of both the piercing needle and the flexible infusion cannula into the tissue, the piercing needle is retracted, while the flexible infusion cannula remains in the tissue. Either a single septum is used for both drug delivery and the introduction of the piercing needle, or alternatively, two different septa may be employed. Typical examples are described in WO 02/07804 A1, U.S. Publication No. 2012/0296290 A1 and EP 2528642 A2.

In order to avoid leakage of the liquid drug and to avoid contamination from the outside, such septa are commonly cylindrically shaped and prestressed by radial compression. In such systems, the septum is built into a cannula housing, which compresses the septum. A further beneficial effect of the radial compression is that after penetration and subsequent removal of the needle or the cannula, the thus generated channel-shaped cut within the septum is compressed and the occurrence of leakage is favorably avoided or at least diminished.

As indicated above, one possible approach to achieve this goal is to prestress the septum by radial compression. However due to constructional constraints, the compression cannot be infinitively increased. Importantly, while radial compression of the septum indeed diminishes leakage of liquid drug in cases in which the septum has been pierced only once, leakage becomes problematic upon repeated piercing events. Furthermore, typical infusion systems employ infusion pumps, which deliver the liquid drug to the patient and therefore a fluidic pressure is exerted. As a result of the fluidic pressure, leakage becomes a severe problem, especially if the septum has been pierced already multiple times.

For the reasons above, septa known in the state of the art can be problematic, in particular with respect to leakage upon piercing, in particular multiple piercing, with a cannula or a needle. Firstly, in case of small dosing units for infusing doses in the nanoliter range, which are typically employed in continuous insulin infusion, any occurring undetected leakage may have a dramatic influence on dosage and thus on the patient's health. Secondly, many automated infusion devices comprise occlusion detection devices which are malfunctioning if operated in an untight system.

SUMMARY

This disclosure teaches an improvement to the state of the art regarding the design and use of elastic septa in the context of infusion and/or injection of liquid drugs, thereby preferably avoiding disadvantages of the prior art fully or partly. The septum may in particular belong to an infusion set as used, for example, in CSII, or a drug reservoir.

In favorable embodiments, the improved septum provides a tight sealing by the septa even if pierced multiple times and/or if exposed to higher pressures.

Further, in advantageous embodiments, the septum can be manufactured in a cost efficient manner.

According to an aspect, a pierceable elastic septum for use in drug reservoirs and infusion sets is disclosed. The pierceable septum comprises a first surface and a second surface, which are positioned opposite to each other. A distance between the first surface and the second surface is not constant over the first surface, and is designed such that if a higher pressure is applied to the first surface as compared to the second surface, a component of a force, which is exerted on the first surface, acts towards an axis which intersects the center of the first surface and the center of the second surface. It is noted that the distance between the first surface and the second surface is not constant over the first surface in both unstressed and stressed states. Consequently, this feature is independent of any external forces and in particular also in the isolated and non-assembled state of the septum. The first surface is any surface of the septum, which is in an operative state exposed to a first pressure exerted by a fluid. This pressure may be higher than atmospheric pressure. In an operative state, the first surface is in contact with, in particular, exposed to, the fluid. In addition, the first surface can comprise edges. The second surface of the septum is exposed to a second pressure, whereby in an operative state, the second pressure is lower than the first pressure. Apart from the first and the second surfaces, the septum can optionally comprise at least one additional surface between the first and the second surface, which can optionally merge into the first surface and/or the second surface, i.e., the first surface and the at least one additional surface are not necessarily separated by an edge. The at least one additional surface differs from the first surface in that in an operative state, it is not exposed to a pressure exerted by a fluid; however, it can be exposed to mechanical pressure. Apart from particular embodiments shown hereinafter, the first surface may generally be planar, apart from a recess, blind hole, groove or a protruding element. The second surface may usually be planar, however a different shape with a recess and a protrusion is also possible.

According to a further aspect, a pierceable elastic septum in an infusion set or a drug reservoir for establishing a fluid connection is disclosed. The fluid connection may be temporary and established by piercing the septum with a cannula or needle. The fluid connection may be established between a liquid drug reservoir and an infusion pump or between a cannula unit and an infusion pump. Additionally, any puncture sites or through-cuts of the septum resulting for example from piercing by a cannula or a needle may be sealed.

As used herein, the term "septum" is readily understood by those skilled in the art and is typically an engineered element, for example in the form of a membrane or plug, for sealingly separating a first side and second side in a fluid, i.e., gas and/or liquid, tight seal, which can be pierced by a needle or a cannula. Typically, a septum does not comprise an opening or a puncture, which passes through the septum from the first side to the second side, before a needle or a cannula has been pierced through the septum. Consequently, a stump needle cannot be easily pierced through the septum without exerting high forces. Apart from the first surface being shaped as explained above and further below, the first and second surface may be coplanar.

As readily understood by those skilled in the art, the expression "a force acting towards an axis" is to be understood as a positive force vector, which has a component directed towards an axis, as opposed to a force acting away from an axis. The angle between such a force vector and an axis is not necessarily 90°, but can also be a different suitable angle. The expression "a force, which is exerted on a surface or applied to a surface" is to be understood as a positive force vector, which has a component directed essentially normal to the surface. In case the surface has a rounded shape, the positive force vector typically has a component directed essentially normal to the tangent at a particular point of the surface.

As readily understood by those skilled in the art, the term "distance" is defined by a straight line connecting two points in space. Therefore, the distance between two surfaces at a given position of one of the surfaces is the length of the shortest possible straight line between the two surfaces at the given position.

In an embodiment, the first surface is designed such that any force or at least a component of a force applied to the first surface, acts transverse, for example perpendicular, towards an axis which intersects the center of the first surface and the center of the second surface.

In an advantageous embodiment, the first surface of the septum comprises one or more recess(es). As readily understood by those skilled in the art, a recess can be a notch, cavity, groove, blind hole and the like. Importantly, a recess is an inherent feature of the septum. Therefore, any recess may be present in the septum in both unstressed and stressed states. The recess is accordingly also presented in the isolated and unassembled state of the septum. If a higher pressure is applied to the first surface as compared to the second surface of such an embodiment in an operated state,
  (i) an axis-directed component of a force which is exerted on the first surface acts towards an axis which intersects the center of the first surface and the center of the second surface, and
  (ii) an edge-directed component of the force which is exerted on the first surface acts opposite to an axis which intersects the center of the first surface and the center of the second surface.

The first surface of the pierceable septum may be shaped in such a way that the distance between the first surface and the second surface at the center of the first surface is larger than a distance between the first surface and the second surface at a different position of the first surface. In typical embodiments, the distance between the first surface and the second surface at the center of the first surface may be larger than a distance between the first surface and the second surface at any different position of the first surface.

In some typical embodiments, the septum is disk-shaped, with the first surface and the second surface of the pierceable septum being of circular contour, resulting in a circular footprint. However, the contour might also be different, e.g., elliptic, or may be angular, such as triangular, rectangular or quadratic. Moreover, the pierceable septum may have the shape of an e.g., cylindrical or cuboid plug. In a typical disk-shaped septum, the diameter of the first surface and the second surface is 2 mm to 6 mm, preferably 3 mm to 4 mm.

In a typical embodiment, the distance between the first surface and the second surface at the center of the first surface is 1 mm to 3 mm, in particular 1 mm to 2 mm.

Advantageously, the pierceable septum can be made of a polymer, preferably an elastic polymer or rubber such as silicone, natural rubber, urethane, or any other type of polymer which has the desired physical and chemical properties. The septum can be manufactured by injection moulding.

In an embodiment, the pierceable septum is prestressed by radial compression. The term "radial compression" as used herein refers to a force which is exerted towards the axis intersecting the center of the first surface and the center of the second surface. Radial compression can for example be induced, in an operational configuration, by a housing, which exerts a force on the septum. Furthermore, the septum can be designed in a way that the septum itself induces radial compression. For example, the septum can comprise multiple coaxial layers, which surround an axis which intersects the center of the first surface and the center of the second surface. In such an embodiment, at least one prestressing layer is constructed in a way that it prestresses an inner layer by radial compression. A prestressing layer can be made from a different material, such as metal or plastic. Preferably, such a layer is built in between elastic polymer layers and is thus at least not fully visible. Such an embodiment combines this disclosure and approaches known in the state of the art in order to reduce leakage. Consequently, the state of the art regarding the design of elastic septa in context of infusion and/or injection of liquid drugs is improved.

In an embodiment, the first surface of the pierceable septum comprises a circumferentially closed groove, which surrounds the center of the first surface, preferably in a circular manner. As readily understood by those skilled in the art, a groove does not completely pass through the septum from the first surface to the second surface. Typically, the ratio of the distance between the first surface and the second surface at the center of the first surface and the depth of the groove is 7:2 to 2:1. Therefore, a typical septum with a distance between the first surface and the second surface at the center of the first surface of 1 mm to 3 mm, may comprise a groove with a depth of 0.4 mm to 0.6 mm. Furthermore, the width of the groove may be in the same range as the depth of the groove. The depth of the groove is defined as smallest distance between the first surface and the second surface at the groove. However, as those skilled in the art will readily understand, the dimensions of the groove are depending on the other dimensions of the septum. In an embodiment, the first surface of the pierceable septum comprises at least two grooves, which are separated from each other and do not merge. For example, two curved grooves might surround the center of the first surface in a half-circular manner, without merging into each other. Alternatively, three or more curved grooves might surround the center of the first surface without merging into each other.

Advantageously, the one or more grooves are symmetrically arranged with respect to a rotational axis.

In some embodiments with one or more grooves, the one or more grooves have a curved cross-section or an angular cross-section. Such an angular cross-section can be triangular, rectangular, quadratic or even trapezoid or rhombic.

In an embodiment, the pierceable septum comprises a plurality of blind holes, for example stud bores, surrounding the center of the first surface. As readily realized by those skilled in the art, the stud bores are not through bores, which means they do not completely pass through the septum from the first surface to the second surface. However, stud bores and blind holes comprise an opening towards the first surface and extend towards the second surface. Preferably, the stud bores and the blind holes surround the center of the surface in a circular manner.

In another embodiment, the first surface of the pierceable septum comprises a protruding part of an elliptic paraboloid. Furthermore, the center of the first surface defines the vertex of the elliptic paraboloid. As used herein, the term elliptic paraboloid is known to the skilled person and defines a three-dimensional geometric body obtained by revolving a two-dimensional parabola around its axis of symmetry. Consequently, when viewed onto the first surface of a septum according to this disclosure a part of an elliptic paraboloid is protruding from the first surface in the direction of the viewer. In such embodiments, a circumferentially closed groove may surround the center of the first surface.

In an embodiment, the pierceable septum is shaped in such a way that an area of the first surface between the edge and the center of the first surface exists, at which the distance between the first surface and the second surface is smaller than the distance between the first surface and the second surface at both the edge and at the center of the first surface. Consequently, in such an embodiment the smallest distance between the first surface and the second surface of the pierceable septum is neither at the edge, nor at the center of the first surface. However this does not mean that the distance between the first surface and the second surface at the edge and at the center of the first surface have to be necessarily equal. Nevertheless, this can be the case. It follows from the above that the pierceable septum may for example comprise a first surface with a circumferentially closed groove. Preferably the cross section of such a groove may be at least partially defined by a protruding part of the elliptic parabloid as disclosed above.

Optionally, in some embodiments, the distance between the first surface and the second surface is essentially at the full area of the first surface between the edge and the center of the first surface smaller than the distance between the first surface and the second surface at the edge or at the center of the first surface. In other words, when viewed onto the first surface, essentially the whole area between the edge and the center of the first surface is directed inwards. As readily understood by those skilled in the art, embodiments in which essentially the whole area between the edge and the center of the first surface is directed inwards also comprise those in which this may not be perfectly met in a strict sense, e.g., due to manufacturing tolerances and/or assembly.

Advantageously, the first surface is shaped in such a way that the first surface is at least partially wavelike in cross-section. If a higher pressure is applied to the first surface as compared to the second surface of such an embodiment in an operated state,
  (i) an axis-directed component of a force which is exerted on the first surface acts towards an axis which intersects the center of the first surface and the center of the second surface, and
  (ii) an edge-directed component of the force which is exerted on the first surface acts opposite to an axis which intersects the center of the first surface and the center of the second surface.

In a further embodiment, the pierceable septum is symmetrical with respect to at least one mirror plane, which is transverse, preferably perpendicular, to the axis intersecting the center of the first surface and the center of the second surface. Consequently, in such an embodiment, the first surface and the second surface are equally shaped.

In another embodiment, the pierceable septum comprises a first outer layer, a middle layer and a second outer layer. The first outer layer comprises the first surface as an outer surface and the second outer layer comprises the second surface as an outer surface. The middle layer is sandwiched between the first and second outer layer. For example, the middle layer may be directly sandwiched between the first and second outer layer or may be indirectly sandwiched between the first and second outer layer. The hardness and/or the elastic modulus of the middle layer is different from the hardness and/or the elastic modulus of the first and second outer layer. Typically, the hardness and/or the elastic modulus of the first and second outer layer are essentially equal. Advantageously, the hardness and/or the elastic modulus of the middle layer is smaller than the hardness and/or the elastic modulus of the first and second outer layer. The hardness of a layer may be defined, e.g., by its Shore hardness. With respect to the preferably employed materials, the Shore A hardness is typically used. The elastic modulus of a layer is a common number in the technical field of material sciences and is used as a measure for the resistance of a material to be deformed elastically. Preferably, the shear modulus is used herein as the elastic modulus. In an embodiment according to this disclosure, the layers are usually configured such that the elastic restoring force of the middle layer is different from the elastic restoring force of the first and second outer layer, i.e., the elastic restoring force of the middle layer can be smaller or larger than the elastic restoring force of the first and second outer layer. As it is known to the person skilled in the art, the elastic restoring force is directly influenced by the hardness and/or the elastic modulus of the layer. Consequently, in the described embodiment, the septum may comprise a first outer layer, a middle layer and a second outer layer, wherein the middle layer may exert a different elastic restoring force upon piercing of the septum with a cannula or a needle than the first and second outer layer. Therefore, upon retraction of the needle an offset may be generated in the channel-shaped cut, which results from the puncture of the needle.

Advantageously, the first outer layer, the middle layer and the second outer layer may be plane-parallel and may preferably be transverse, typically perpendicular to the axis which intersects the center of the first surface and the center of the second surface. For example, the contact surface of the layers may be plane-parallel and/or be transversal, typically perpendicular to the axis which intersects the center of the first surface and the center of the second surface.

Alternatively, the first surface of the pierceable septum is conical or hemispherical. Consequently, the thickness of the septum, i.e., the distance between the first surface and the second surface, declines from the center of the first surface to an edge of the septum. Optionally, such a septum can also be essentially conical or hemispherical and still comprise one or more grooves or blind holes.

According to a further aspect, a pierceable elastic septum for use in drug reservoirs and infusion sets is provided, wherein the septum comprises a first outer layer, a middle layer and a second outer layer. The middle layer is sandwiched between the first and the second outer layer. The middle layer may even be directly sandwiched between the first and the second outer layer. The hardness and/or the elastic modulus of the middle layer is different from the hardness and/or the elastic modulus of the first and second outer layer. The first outer layer may comprise a first surface as an outer surface and the second layer a second surface as the outer surface. Both the first surface and the second surface may be essentially flat and/or plane-parallel. However, the first surface and the second surface may also be shaped and/or designed according to the other aspect of this disclosure as described above. For example, the first surface may at least partially be wavelike in cross-section. Typically, the hardness and/or the elastic modulus of the first and second outer layer are essentially equal. Advantageously, the hardness and/or the elastic modulus of the middle layer is smaller than the hardness and/or the elastic modulus of the first and second outer layer. The hardness of a layer may be defined, e.g., by its Shore hardness. With respect to the preferably employed materials, the Shore A hardness is typically used. Typically, the layers are configured such that the elastic restoring force of the middle layer is different from the elastic restoring force of the first and second outer layer, i.e., the elastic restoring force of the middle layer can be smaller or larger than the elastic restoring force of the first and second outer layer. As it is known to the person skilled in the art, the elastic restoring force is directly influenced by the hardness and/or the elastic modulus of the layer. Consequently, the septum may comprise a first outer layer, a middle layer and a second outer layer, wherein the middle layer may exert a different elastic restoring force upon piercing of the septum with a cannula or a needle than the first and second outer layer. Therefore, upon retraction of the needle an offset may be generated in the channel-shaped cut, which results from the puncture of the needle.

According to a further aspect, an infusion set which comprises a pierceable septum is provided in accordance to the present disclosure. The pierceable septum is built into a housing unit which forms part of the infusion set and which might prestress the septum by radial compression. The infusion set may comprise a cannula unit with a possibly pressurized compartment, which is at least partially formed by the first surface of the septum and is configured to comprise a liquid drug. The liquid drug can for example be pumped under pressure into the compartment by an infusion pump. In particular, the infusion pump can be fluidly connected to a tubing, which can comprise a connector device for connecting with the cannula unit. The connector device typically comprises a connector cannula, which is pierced through the septum in an operative state. Hence, a fluid connection between the pump and the compartment, which is at least partially formed by the septum, is established. The compartment can further be fluidly connected or temporarily fluidly connected to the patient's tissue via a rigid or soft infusion cannula. The connector device of the tubing is favorably configured to be removably engaged and thereby connected to a corresponding counter connector device of the cannula unit, for example via releasable snap fit or bayonet connection. The septum may be arranged in a center of the counter-connector device and pierced by the connector cannula of the connector device. While such an arrangement is in principle known in the art, the use of a septum in accordance with this disclosure is particularly favorable in this context since it allows multiple coupling and decoupling sequences while avoiding or at least reducing the occurrence of septum leakages.

According to a still further aspect, a drug reservoir, for example, an insulin cartridge or a drug bag, which comprises a septum is taught according to this disclosure. The reservoir can, apart from the septum design, be a commonly employed insulin cartridge as known in the art and widely available or customly manufactured. The reservoir can further be configured to effect prestressing of the septum by radial compression.

BRIEF DESCRIPTION OF THE DRAWINGS

The above-mentioned aspects of exemplary embodiments will become more apparent and will be better understood by reference to the following description of the embodiments taken in conjunction with the accompanying drawings, wherein:

FIG. 1 (*b*) shows a plan view of a first surface of a pierceable septum in accordance to one embodiment of this disclosure;

FIG. 1 (*c*) shows a plan view of a first surface of a pierceable septum in accordance to another embodiment of this disclosure;

FIG. 10 (a) shows a cross-sectional view of a pierceable septum built into a housing in accordance to another embodiment of this disclosure;

FIG. 10 (b) shows a cross-sectional view of a pierceable septum built into a housing in accordance to another embodiment of this disclosure;

FIG. 12 (a) shows a cross-sectional view of a pierceable septum built into a housing in accordance to another embodiment of this disclosure;

FIG. 12 (b) shows a cross-sectional view of a pierceable septum built into a housing in accordance to another embodiment of this disclosure.

DESCRIPTION

The embodiments described below are not intended to be exhaustive or to limit the invention to the precise forms disclosed in the following detailed description. Rather, the embodiments are chosen and described so that others skilled in the art may appreciate and understand the principles and practices of this disclosure.

Figure 1:
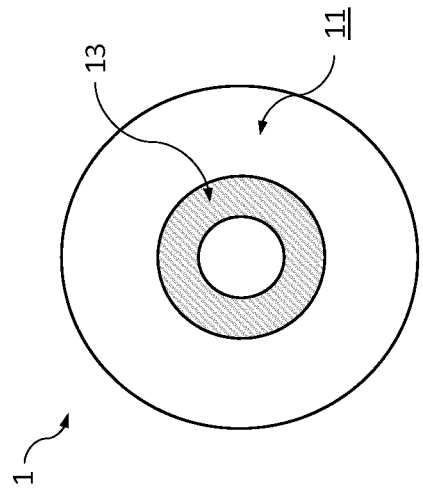
FIG. 1 (*a*) shows a cross-sectional view of a pierceable septum in accordance to one embodiment of this disclosure.
Figure 1:
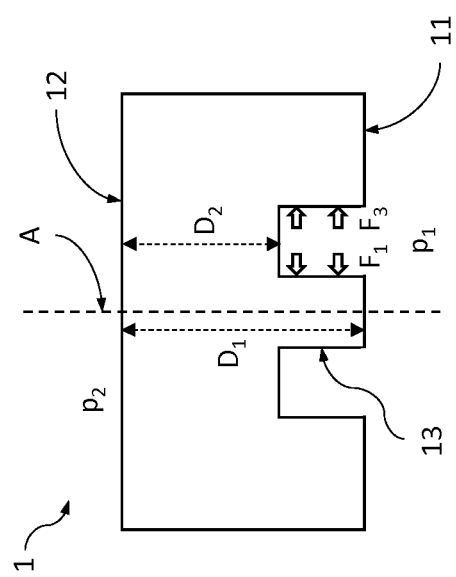

An advantageous embodiment of a pierceable septum 1 according to this disclosure is shown in FIG. 1 (a). The pierceable septum 1, displayed in a cross-sectional view, comprises a first surface 11 and a second surface 12, which are positioned opposite to each other. As exemplified by distances $D_1$ and $D_2$, the distance between the first surface and the second surface is not constant over the first surface. The distance between the first surface and the second surface as a function of the diameter (radial distance from axis A) is designed such that if a pressure $p_1$ is applied to the first surface, which is higher than a pressure $p_2$ applied to the second surface, a component $F_1$ of a force, which is exerted on the first surface, acts towards an axis A intersecting the center of the first surface 11 and the center of the second surface 12. In the particular embodiment shown, a component of force $F_1$ can act transversely, towards axis A. In addition, a component $F_3$ of a force, which is exerted on the first surface, acts opposite to an axis which intersects the center of the first surface and the center of the second surface. As readily realized by those skilled in the art, the component $F_1$ is axis-directed and leads to compression of the septum at the center of the first surface 11, while the component $F_3$ is edge-directed and leads to an expansion of the septum at the edges of the first surface 11.

In the embodiment of FIG. 1 (a), the first surface 11 comprises a groove 13 having a rectangular cross-section, which circumferentially surrounds the center of the first surface 11. FIG. 1 (b) represents a plan view of the first surface 11 comprising a groove 13, which circumferentially surrounds the center of the first surface 11 in a circular manner and which is symmetrically arranged with respect to a rotational axis. FIG. 1 (c), displays another embodiment of this disclosure as a plan view of the first surface 11. Therein, the first surface 11 of the pierceable septum 1 comprises two grooves 13a and 13b surrounding the center of the first surface in a half-circular manner, without merging into each other. In this particular embodiment, the two grooves are symmetrically arranged with respect to a rotational axis. However, the grooves could also be arranged in an asymmetrical manner. In both the embodiments of FIG. 1 (a, b) and FIG. 1 (c), the first surface 11 is stepped with the distance between the first surface 11 and the second surface 12 being either $D_1$ or $D_2$ for each point.

Figure 2:
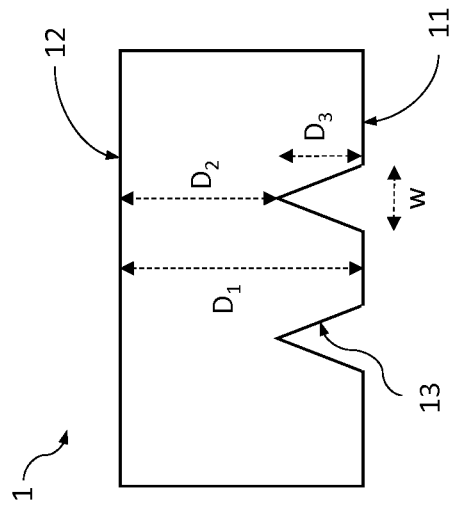
FIG. 2 shows a cross-sectional view of a pierceable septum in accordance to another embodiment of this disclosure.
Figure 1:
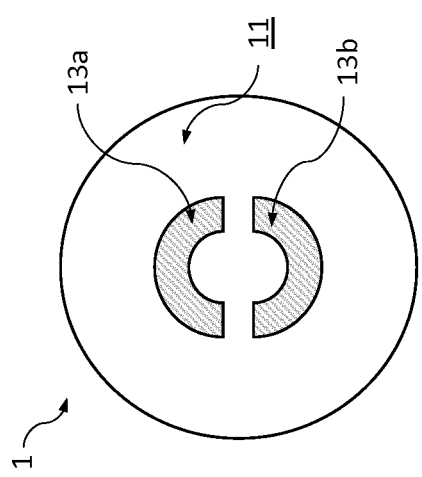

FIG. 2 shows another embodiment of a pierceable septum 1 according to this disclosure. As can be seen from the cross-sectional view of septum 1, the first surface 11 comprises a circumferential groove 13 which has a triangular cross-section. Moreover, the shape of the first surface of the septum is shaped in such a way, that the distance $D_1$ between the first surface 11 and the second surface 12 at the center of the first surface is larger than a distance $D_2$ between the first surface and the second surface at a different position of the first surface. Here, the distance between the first surface 11 and the second surface 12 varies continuously from $D_1$ at the edges to $D_2$ at the center of the groove 13. Groove 13 has a depth $D_3$ and a width w.

Figure 3:
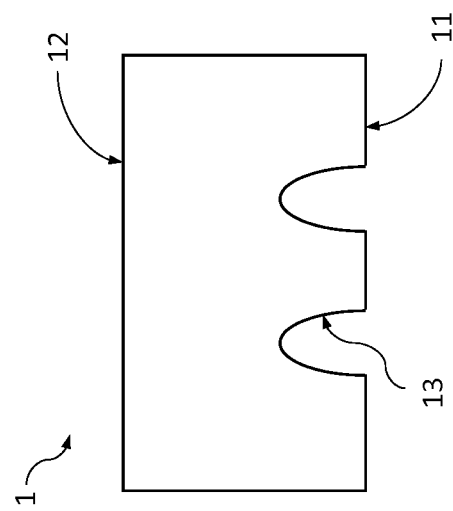
FIG. 3 shows a cross-sectional view of a pierceable septum in accordance to another embodiment of this disclosure.

FIG. 3 shows another embodiment of a pierceable septum 1 according to this disclosure, wherein the first surface comprises a circumferential groove 13 which has a curved cross-section, also resulting in a continuous change in the distance between first surface 11 and the second surface 12.

Figure 4:
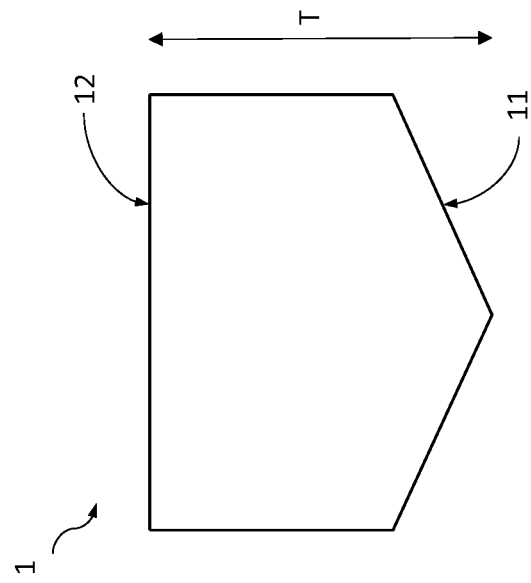
FIG. 4 shows a cross-sectional view of a pierceable septum in accordance to another embodiment of this disclosure.

The septum shown in FIG. 4 represents another advantageous embodiment of this disclosure. Therein, the first surface 11, positioned opposite to second surface 12, is conical. The thickness T of the septum declines from the center of the first surface to an edge.

Figure 5:
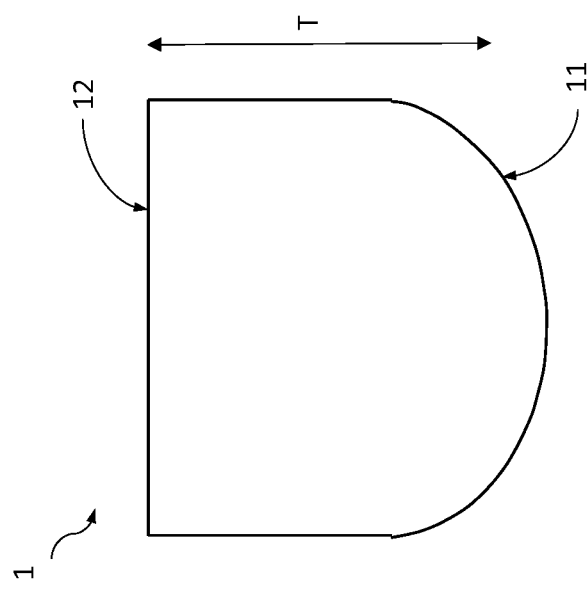
FIG. 5 shows a cross-sectional view of a pierceable septum in accordance to another embodiment of this disclosure.

The septum shown in FIG. 5 represents another embodiment of this disclosure. Therein, the first surface 11, which is positioned opposite to the second surface 12 is hemispherical. As in case of FIG. 4, the thickness T declines from the center of the first surface to an edge.

Figure 6:
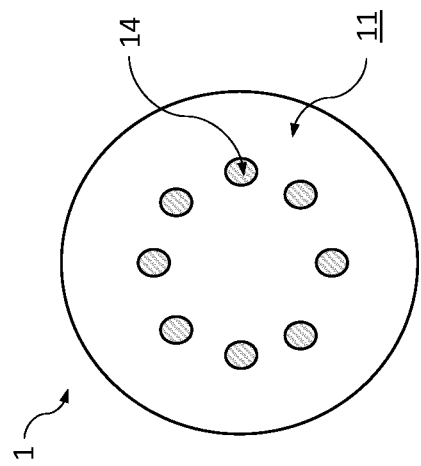
FIG. 6 shows a plan view of a first surface of a pierceable septum in accordance to another embodiment of this disclosure.

FIG. 6 shows a top view of the first surface 11 of another embodiment of a pierceable septum 1. The first surface 11 comprises a plurality of blind holes 14, which surrounds the center of the first surface in a circular manner.

Figure 7:
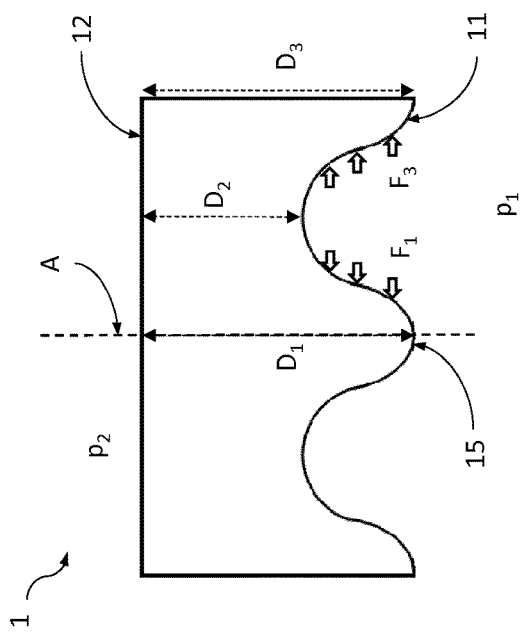
FIG. 7 shows a cross-sectional view of a pierceable septum in accordance to one embodiment of this disclosure.

Another advantageous embodiment of a pierceable septum 1 according to this disclosure is shown in FIG. 7. The pierceable septum 1, displayed in cross-sectional view, comprises a first surface 11 and a second surface 12, which are positioned opposite to each other. As exemplified by distance $D_1$ and $D_2$, the distance between the first surface 11 and the second surface 12 is not constant over the first surface 11. The distance between the first surface 11 and the second surface 12 as a function of the diameter (radial distance from axis A) is designed such that if a pressure $p_1$ is applied to the first surface, which is higher than a pressure $p_2$ applied to the second surface, a component $F_1$ of a force which is exerted on the first surface acts towards an axis A intersecting the center of the first surface 11 and the center of the second surface 12. In addition, a component $F_3$ of a force which is exerted on the first surface acts opposite to an axis which intersects the center of the first surface and the center of the second surface, i.e., a component $F_3$ can act away from an axis which intersects the center of the first surface and the center of the second surface. As readily realized by those skilled in the art, the component $F_1$ is axis-directed and leads to compression of the septum at the center of the first surface 11, while the component $F_3$ is edge-directed and leads to an expansion of the septum at the edge of the first surface 11. In the embodiment shown, the first surface 11 comprises a protruding part 15 of an elliptic paraboloid. As readily seen, the center of the first surface defines the vertex of the paraboloid. Furthermore, as indicated by distance $D_2$, the pierceable septum shown is shaped in such a way that an area exists at which the distance between the first surface 11 and the second surface 12 is smaller than the distance between the first surface 11 and the second surface 12 at the edge (see $D_3$) and at the center of the first surface (see $D_1$). In this particular embodiment, the distance between the first surface 11 and the second surface 12 is at the full area of the first surface between the edge and the center of the first surface 11 smaller than the distance between the first surface 11 and the second surface 12 at the edge and at the center of the first surface 11. It can be further seen from FIG. 7, that the first surface 11 of the pierceable septum may comprise a circumferentially closed groove with a curved cross section and the first surface 11 is at least partially wavelike in cross-section.

Figure 8:
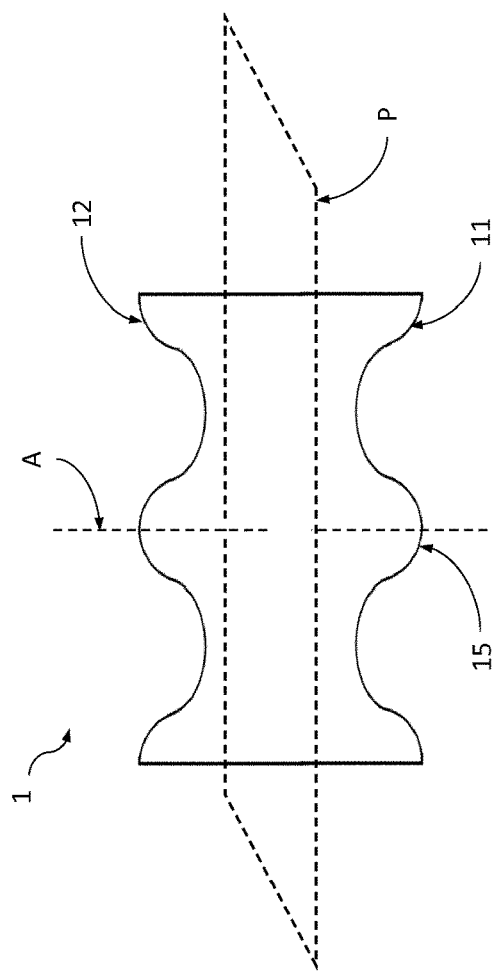
FIG. 8 shows a cross-sectional view of a pierceable septum in accordance to another embodiment of this disclosure.

FIG. 8 shows another embodiment of a pierceable septum 1 according to this disclosure, wherein the septum is symmetrical with respect to mirror plane P. The mirror plane P is perpendicular to axis A. The axis A intersects the center of the first surface 11 and the center of the second surface 12. As a consequence of the symmetrical configuration, the first surface 11 and the second surface 12 each comprise a protruding part 15 of an elliptic paraboloid and are equally shaped.

Figure 9:
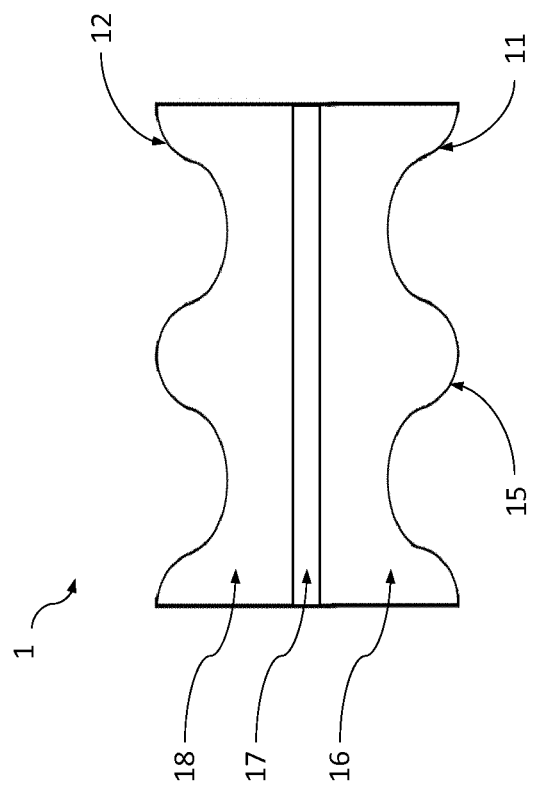
FIG. 9 shows a cross-sectional view of a pierceable septum in accordance to another embodiment of this disclosure.

FIG. 9 shows another embodiment of a pierceable septum 1 according to this disclosure. The septum 1 comprises three layers, first outer layer 16, middle layer 17 and second outer layer 18. The first outer layer 16 comprises the first surface 11 as an outer surface and the second outer layer 18 comprises the second surface 12 as an outer surface. As can be seen, the middle layer 17 is sandwiched between the first outer layer 16 and the second outer layer 18. In this particular septum shown, the contact surfaces of the three layers are plane-parallel and transversal to the axis which intersect the center of the first surface 11 and the center of the second surface 12. Such design with a middle layer 17 is not limited to a particular embodiment of the septum 1 but may also be used in the context of other embodiments, such as an embodiment according to FIG. 7.

FIG. 10 (a) depicts a pierceable septum 1 according to this disclosure, which is built into a housing unit 20. The housing unit 20 is part of a cannula unit 25, which can be part of an infusion set. Additionally, cannula unit 25 may comprise a flexible infusion cannula 23 which can be inserted into the patient's tissue by insertion of a piercing needle through the septum, prior to assembly of removable connector device 24. As can be readily seen, the housing unit 20 and the septum form a compartment 22, which can comprise a liquid drug. For example, the drug can be pumped under pressure into compartment 22 by an infusion pump (not shown) which is in fluid connection with connector cannula 21. Connector cannula 21 is part of connector device 24, which is removably connected to cannula unit 25 and not depicted in greater detail. In this particular embodiment, a force $F_1$ might emanate from a fluid pressure $p_1$ within compartment 11. As indicated by the arrows, an axis-directed component $F_1$ of the force applied to the first surface acts towards an axis (not shown in FIG. 10 (a), see FIG. 1 (a)) which intersects the center of the first surface and the center of the second surface. As a result, the septum 1 is compressed at the center of the first surface and engages connector cannula 21. In addition, an edge-directed component $F_3$ of a force, which is exerted on the first surface, acts opposite to an axis which intersects the center of the first surface and the center of the second surface, thereby ensuring sealing engagement between the housing 20 and the peripheral edge of first surface 11. Additionally, as indicated by the arrows the pierceable septum 1 is exposed to a force $F_2$, by being prestressed by radial compression. Advantageously, the piercing of septum 1 does not lead to any leakage occurring between the walls of the cannula or the needle, because a component $F_1$ of a force acts towards the connector cannula and also towards an axis, which intersects the center of the first surface and the center of the second surface. In addition, while a second force $F_2$ acts toward the same axis, a third force $F_3$ acts opposite to this axis, which results in a particular tight sealing between housing 20 and septum 1.

FIG. 10 (b) depicts cannula unit 25 with pierceable septum 1, built into housing unit 20. However the connector device (see 24 in FIG. 10(a)) comprising a connector cannula (see 21 in FIG. 10(a)) has been removed and thus disconnected from the cannula unit 25. As indicated by curved line 26, the removal of the connector cannula led to the formation of a through-cut or a puncture in the septum. This through-cut or puncture is now sealingly closed, as firstly a component $F_1$ of a force acts towards an axis, which intersects the center of the first surface and the center of the second surface and secondly as a second force $F_2$ acts toward the same axis.

Figure 11:
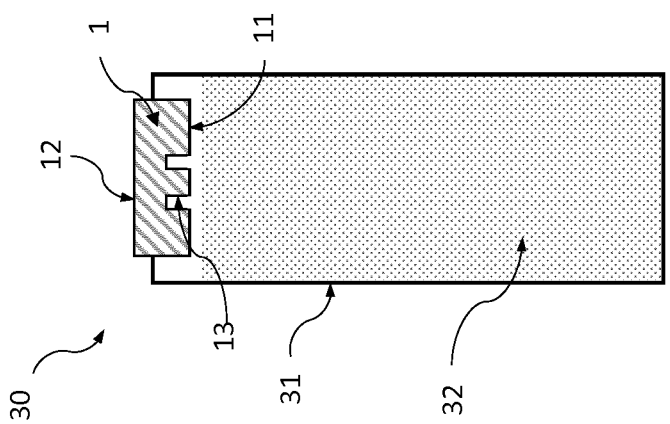
FIG. 11 shows a cross-sectional view of a reservoir for drugs comprising a septum in accordance to another embodiment of this disclosure.

FIG. 11 shows a reservoir for drugs 30, for example an insulin cartridge comprising a walls 31 and liquid drug 32. A pierceable septum 1 according to this disclosure allows to withdraw drug 32 from the reservoir by a cannula and ensures tight sealing of the pierced septum 1 after removal of the cannula. The particular septum shown in FIG. 11 comprises second surface 12 and first surface 11 with a circumferential groove.

FIG. 12 (a) depicts a pierceable septum 1 according to this disclosure, which is built into a housing unit 20. The housing unit 20 is part of a cannula unit 25, which can be part of an infusion set. Additionally, cannula unit 25 may comprise a flexible infusion cannula 23 which can be inserted into the patient's tissue by insertion of a piercing needle through the septum, prior to assembly of removable connector device 24. As can be readily seen, the housing unit 20 and the septum form a compartment 22, which can comprise a liquid drug. For example, the drug can be pumped under pressure into compartment 22 by an infusion pump (not shown) which is in fluid connection with connector cannula 21. Connector cannula 21 is part of connector device 24, which is removably connected to cannula unit 25 and not depicted in greater detail. In this particular embodiment, a force might emanate from a fluid pressure $p_1$ within compartment 22. As indicated by the arrows, an axis-directed component $F_1$ of the force applied to the first surface acts towards an axis (not shown in FIG. 12 (a), see FIG. 7) which intersects the center of the first surface and the center of the second surface. As a result, the septum 1 is compressed at the center of the first surface and engages connector cannula 21. In addition, an edge-directed component $F_3$ of a force, which is exerted on the first surface, acts opposite to an axis which intersects the center of the first surface and the center of the second surface, thereby ensuring sealing engagement between the housing 20 and the peripheral edge of first surface 11. Additionally, as indicated by the arrows, the pierceable septum 1 is exposed to a force $F_2$, by being prestressed by radial compression. Advantageously, the piercing of septum 1 does not lead to any leakage occurring between the walls of the cannula or the needle, because a component $F_1$ of a force acts towards the connector cannula and also towards an axis, which intersects the center of the first surface and the center of the second surface. In addition, while a second force $F_2$ acts toward the same axis, a third force $F_3$ acts opposite to this axis, which results in a particular tight sealing between housing 20 and septum 1.

FIG. 12 (b) depicts cannula unit 25 with pierceable septum 1, built into housing unit 20. However the connector device (see 24 in FIG. 4(a)) comprising a connector cannula (see 21 in FIG. 12 (a)) has been removed and thus disconnected from the cannula unit 25. As indicated by curved line 26, the removal of the connector cannula led to the formation of a through-cut or a puncture in the septum. This through-cut or puncture is now sealingly closed, as firstly a component $F_1$ of a force acts towards an axis, which intersects the center of the first surface and the center of the second surface and secondly as a second force $F_2$ acts toward the same axis.

Figure 13:
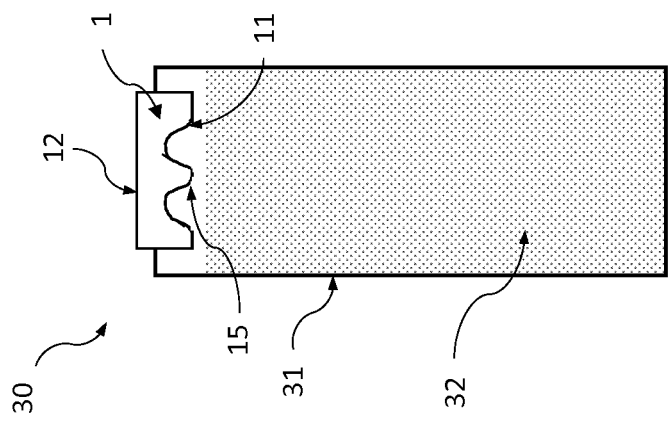
FIG. 13 shows a cross-sectional view of a reservoir for drugs comprising a septum in accordance to another embodiment of this disclosure.

FIG. 13 shows a reservoir for drugs 30, for example an insulin cartridge comprising walls 31 and liquid drug 32. A pierceable septum 1 according to this disclosure allows to withdraw drug 32 from the reservoir by a cannula and ensures tight sealing of the pierced septum 1 after removal of the cannula. The particular septum shown in FIG. 13 comprises second surface 12 and first surface 11 with a protruding part of an elliptic paraboloid 15.

While exemplary embodiments have been disclosed hereinabove, the present invention is not limited to the disclosed embodiments. Instead, this application is intended to cover any variations, uses, or adaptations of this disclosure using its general principles. Further, this application is intended to cover such departures from the present disclosure as come within known or customary practice in the art to which this invention pertains and which fall within the limits of the appended claims.

What is claimed is:

1. A pierceable elastic septum for use in drug reservoirs and infusion sets, comprising:
   first and second surfaces positioned opposite to each other, wherein the first surface comprises a groove disposed around a center of the first surface and an outermost peripheral edge of the septum defines a total area bounded by the outermost peripheral edge wherein the second surface is a single planar surface that fills the entirety of the total area bounded by the outermost peripheral edge;
   a varying distance between the first surface and the second surface configured such that when a higher pressure is applied to the first surface than the second surface, a component of a force exerted on the first surface acts towards an axis (A) which intersects the center of the first surface and a center of the second surface; and
   a housing defining a compartment for a liquid drug wherein the septum is mounted on the housing in an unpierced condition with the first surface of the septum facing the compartment.

2. The pierceable septum according to claim 1, wherein the groove is circular.

3. The pierceable septum according to claim 1, wherein the groove is symmetrically arranged with respect to the axis (A).

4. The pierceable septum according to claim 1, wherein the groove has a cross-section selected from the group consisting of angular, rectangular, quadratic and triangular.

5. The pierceable septum according to claim 1, wherein the varying distance between the first surface and the second surface defines a maximum distance between the first surface and the second surface at the center of the first surface.

6. The pierceable septum according to claim 1, wherein the septum is prestressed by radial compression.

7. The pierceable septum according to claim 1, wherein a plurality of blind holes surrounds the center of the first surface.

8. The pierceable septum according to claim 7 wherein the plurality of blind holes surrounds the center of the first surface in a circular manner.

9. The pierceable septum according to claim 1, wherein, in an unpierced condition, the first surface is conical or hemispherical and the thickness (T) of the septum declines from the center of the first surface to an outer peripheral edge of the septum.

10. The pierceable septum according to claim 1, wherein, in an unpierced condition, the first surface comprises a protruding part of an elliptic paraboloid and wherein the center of the first surface defines the vertex of the elliptic paraboloid.

11. The pierceable septum according to claim 10, wherein, in the unpierced condition, the septum is shaped such that the distance between the first surface and the second surface in an area of the first surface between an outer peripheral edge of the septum and the center of the first surface is smaller than the distance between the first surface and the second surface at both the outer peripheral edge of the septum and at the center of the first surface.

12. The pierceable septum according to claim 11, wherein, in the unpierced condition, the distance between the first surface and the second surface at the outer peripheral edge of the septum and at the center of the first surface are both greater than the distance between the first surface and the second surface for all of the area of the first surface between the outer peripheral edge of the septum and the center of the first surface.

13. The pierceable septum according to claim 1, wherein the first surface is at least partially wavelike in cross-section.

14. The pierceable septum according to claim 1, wherein the septum is symmetrical with respect to at least one mirror plane (P), wherein the mirror plane (P) is transverse or perpendicular to the axis (A) which intersects the center of the first surface and the center of the second surface.

15. The pierceable septum according to claim 1, wherein:
   the septum comprises a first outer layer having the first surface as an outer surface, a second outer layer having the second surface as an outer surface, and middle layer sandwiched between the first and second outer layers; and
   the hardness and/or the elastic modulus of the middle layer is different from the hardness and/or the elastic modulus of the first and second outer layers.

16. The pierceable septum of claim 15, wherein the hardness and/or the elastic modulus of the middle layer is smaller than the hardness and/or the elastic modulus of the first and second outer layers.

17. An infusion set comprising a septum according to claim 1 wherein the infusion set comprises an infusion cannula in communication with the compartment and extending from the housing and a connector device removably connectable to the housing wherein the connector device includes a connector cannula through which the liquid drug is pumped into the compartment such that the liquid drug exerts a fluid pressure on the first surface that acts towards the axis (A).

18. The infusion set according to claim 17, wherein the septum is positioned opposite the infusion cannula and is prestressed by radial compression.

19. A reservoir for a liquid drug comprising a septum according to claim 1 wherein the compartment defines an interior volume of the reservoir, the liquid drug being disposed in the interior volume.

20. The reservoir according to claim 19, wherein the septum is prestressed by radial compression.

21. A method of using a pierceable septum, comprising:
(a) providing a septum having first and second surfaces positioned opposite to each other, the first surface having a groove disposed around a center of the first surface and wherein an outermost peripheral edge of the septum defines a total area bounded by the outermost peripheral edge wherein the second surface is a single planar surface that fills the entirety of the total area bounded by the outermost peripheral edge;
(b) mounting the septum to a housing defining a compartment for a liquid drug wherein the septum is mounted on the housing in an unpierced condition with the first surface of the septum facing the compartment;
(c) piercing the septum with a cannula needle in a location near a center of the septum;
(d) applying fluid pressure to the first surface, the fluid pressure generating
  (i) a central force ($F_1$) directed from the groove toward a center axis (A) of the septum, thereby compressing the septum in the location near the center of the septum pierced by the cannula needle; and
  (ii) a peripheral force ($F_3$) directed from the groove outwardly toward an outer periphery of the septum, whereby the septum at the outer periphery of the septum compresses against the housing in which the septum is disposed.

22. The method of claim 21, further comprising removing the cannula needle and sealing the septum with application of the central force ($F_1$).

23. The method of claim 21, further comprising applying a housing force ($F_2$) from the housing toward the axis (A) to thereby enhance the seal between the housing and the outer periphery of the septum.

24. The method of claim 21, wherein a distance between the first surface and the second surface defines a maximum distance between the first surface and the second surface at the center of the first surface.

\* \* \* \* \*